(12) United States Patent
Yamamoto et al.

(10) Patent No.: US 6,322,517 B1
(45) Date of Patent: Nov. 27, 2001

(54) ELECTRONIC SPHYGMOMANOMETER CAPABLE OF ADJUSTING PRESSURE RELEASE RATE DURING MEASUREMENT

(75) Inventors: Norihito Yamamoto; Toshio Ohtani; Yoshinori Miyawaki; Tomoki Kitawaki, all of Kyoto (JP)

(73) Assignee: Omron Corporation, Kyoto (JP)

( * ) Notice: Subject to any disclaimer, the term of this patent is extended or adjusted under 35 U.S.C. 154(b) by 0 days.

(21) Appl. No.: 09/559,323

(22) Filed: Apr. 27, 2000

(30) Foreign Application Priority Data

Apr. 28, 1999 (JP) .................................... 11-121325

(51) Int. Cl.[7] ....................................................... A61B 5/00
(52) U.S. Cl. .......................... 600/494; 600/496; 600/490; 600/495
(58) Field of Search .................................... 600/485, 450, 600/493–6, 500

(56) References Cited

U.S. PATENT DOCUMENTS

| | | |
|---|---|---|
| 3,452,744 | 7/1969 | Van den Nieuwenhof . |
| 4,625,277 * | 11/1986 | Pearce et al. .................... 600/493 |
| 4,660,567 * | 4/1987 | Kaneko et al. .................. 600/495 |
| 4,671,290 | 6/1987 | Miller et al. . |
| 4,872,461 | 10/1989 | Miyawaki . |
| 5,135,003 * | 8/1992 | Souma ............................. 600/493 |
| 5,467,772 * | 11/1995 | Souma ............................. 600/494 |

FOREIGN PATENT DOCUMENTS

| | | |
|---|---|---|
| 0 134 319 | 3/1985 | (EP) . |
| 0 154 995 | 9/1985 | (EP) . |
| 57-5540 | 1/1982 | (JP) . |
| WO 92/22241 | 12/1992 | (WO) . |

* cited by examiner

*Primary Examiner*—Robert L. Nasser
(74) *Attorney, Agent, or Firm*—Morrison & Foerster LLP (57) ABSTRACT

An electronic sphygmomanometer starts from pressurization and then enters a decompression process. When measurement of blood pressure starts, only a standard pressure release rate voltage is applied to a valve from a standard pressure release rate voltage supply circuit through a decompression control circuit. The valve allows air to be discharged slowly at the standard pressure release rate. If the pressure release rate should be increased for decompression, target pressure release rate acceleration value voltage according to the position of a dial is supplied from an external control signal supply unit. The standard pressure release rate voltage is added to the target voltage and the resultant voltage is supplied to the valve via the decompression control circuit. The valve increases the pressure release rate by the amount corresponding to the external control signal voltage. In this case, even if the dial is returned to zero position, the pressure release rate never falls below the standard pressure release rate.

6 Claims, 11 Drawing Sheets

— BASE POSITION

FIG.7B

SLIDE = ACCELERATE

FIG.7C

RETURN

| t11 | 0.2 |
|---|---|
| t12 | 0.3 |
| t13 | 0.3 |
| t14 | 0.4 |
| ⁓ | ⁓ |
| t21 | 0.2 |

ELECTRONIC SPHYGMOMANOMETER CAPABLE OF ADJUSTING PRESSURE RELEASE RATE DURING MEASUREMENT

BACKGROUND OF THE INVENTION

1. Field of the Invention

The present invention relates to electronic sphygmomanometers, and particularly to an electronic sphygmomanometer capable of adjusting the pressure release rate of a cuff during measurement.

2. Description of the Background Art

One of sphygmomanometers which have long been well-known is a mercury type sphygmomanometer. By such a mercury sphygmomanometer, pressure is applied to a cuff so as to pressurize a blood vessel. In a following decompression process in which air is discharged from the cuff to release the pressure therefrom, drop of mercury is watched, the systolic pressure or maximum blood pressure is determined by detection of K (Korotkoff) sounds with a stethoscope by a person who measures (e.g. physician) and the diastolic pressure or the minimum blood pressure is determined by ceasing of the K-sounds. There is also an electronic sphygmomanometer which electronically measures blood pressure by detecting K-sounds with a sensor.

In the decompression process of these sphygmomanometers, the air is discharged relatively slowly, in other words, the air discharge rate is slow, in order to ensure and facilitate detection of K-sounds. However, the slow air discharge rate prolongs the period from detection to ceasing of K-sounds and accordingly measurement takes too much time, which would cause pain to a subject person. Therefore, when a skilled operator who measures takes blood pressure measurement by using the mercury sphygmomanometer, the operator decreases the cuff pressure first at a constant pressure release rate to determine the systolic pressure by the first occurring K-sounds, then opens an air vent valve to temporarily increase the pressure release rate and accordingly decrease the pressure immediately to a pressure slightly higher than an expected diastolic pressure, and closes the air vent valve to decrease the pressure release rate to reduce the cuff pressure and thus determine the diastolic pressure by confirming ceasing of K-sounds.

Some electronic sphygmomanometers detect K-sounds in a decompression process in which the air is discharged at a slow rate and accordingly determine the systolic pressure by a corresponding cuff pressure, then increase the pressure release rate to a constant fast rate so as to decrease the pressure to the one slightly higher than an expected diastolic pressure, and thereafter return the pressure release rate to the original slow rate and accordingly confirm ceasing of K-sounds to determine the diastolic pressure (see Japanese Patent Publication No. 57-5540).

The pressure release rate of the conventional mercury sphygmomanometer is adjusted directly by manual rotation of a dial in order to control the degree of opening of the air vent valve. After the pressure release rate is increased, if the valve is excessively closed in order to lower the rate to the original slow rate, the decompression could be stopped or the rate could be too slow resulting in a prolonged measurement time. In this case, much skill could be required for measurement. On the other hand, the electronic sphygmomanometer switches the pressure release rate based on a preset cuff pressure with respect to a preset pressure release rate. Therefore, a skilled operator cannot select a pressure release rate based on the operator's experience or according to a subject person.

SUMMARY OF THE INVENTION

One object of the present invention is to provide an electronic sphygmomanometer having a pressure release rate which is easily adjustable by a person not skilled in the art and is freely adjustable for shortening measurement time.

An electronic sphygmomanometer according to one aspect of the present invention applies pressure to a cuff for pressurizing a blood vessel and then measures blood pressure in a decompression process. The electronic sphygmomanometer includes a manual operation unit to electronically control a pressure release rate controller in response to operation thereof.

The electronic sphygmomanometer pressurizes the cuff and thereafter enters the decompression process. In the decompression process, air is slowly discharged at first at a predetermined pressure release rate (e.g. 2 to 3 mmHg/sec). In this process, the manual operation unit is operated to electronically control the pressure release rate controller. The pressure release rate can thus be increased, for example, to the one higher (e.g. 10 mmHg/sec) than the predetermined pressure release rate by one-touch operation.

The manual operation unit is provided to start the decompression process at a predetermined pressure release rate and to manually adjust the pressure release rate to the one higher than the predetermined rate. Therefore, acceleration adjustment is possible without lowering the pressure release rate below the predetermined rate. Consequently, the pressure release rate can be adjusted easily to a higher rate even by a person not skilled in the art. By the degree and time of manual operation of the manual operation unit, the adjustment for increasing the pressure release rate can be made freely based on the experience of an operator and according to a subject person.

An electronic sphygmomanometer according to another aspect of the present invention includes a cuff for pressurizing a blood vessel, a pressurization unit for applying pressure to the cuff, a cuff pressure detector for detecting cuff pressure, an air discharge unit for discharging air from the cuff to release pressure therefrom, a display unit for displaying the cuff pressure, and a manual operation unit which is manually operated for electronically controlling the air discharge unit in response to the manual operation. The manual operation unit is operated to adjust the degree of discharging the air by the air discharge unit.

When an operator measures blood pressure by using this electronic sphygmomanometer while placing a stethoscope on an appropriate site, the pressure release rate controller can be controlled electronically by one-touch operation of the manual operation unit in order to speedily discharge the air after K-sounds are detected. Accordingly, any person can measure blood pressure without special training.

The foregoing and other objects, features, aspects and advantages of the present invention will become more apparent from the following detailed description of the present invention when taken in conjunction with the accompanying drawings.

DESCRIPTION OF THE PREFERRED EMBODIMENTS

Figure 1:
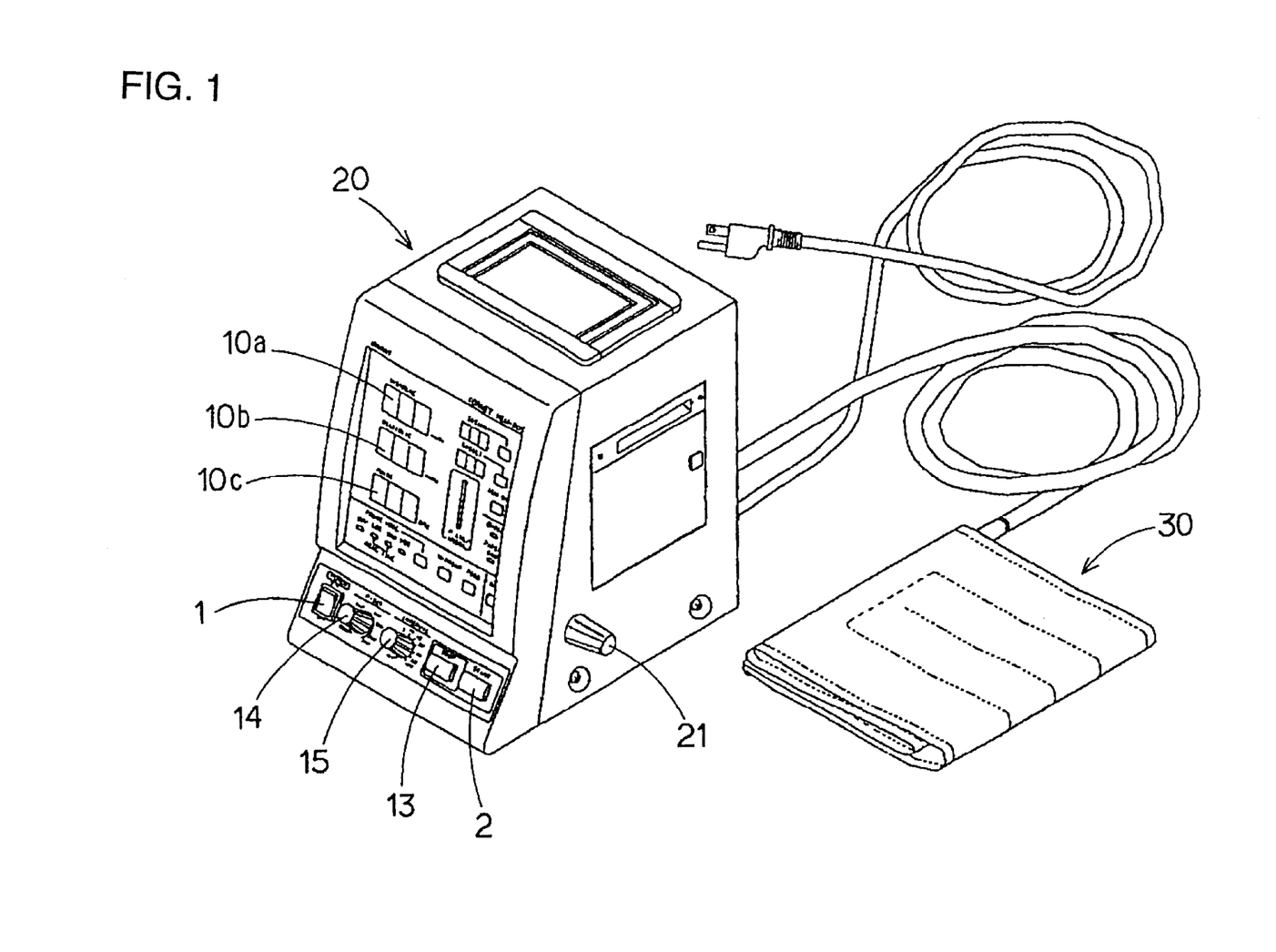
FIG. 1 is a perspective view of an electronic sphygmomanometer according to one embodiment of the present invention.

The present invention is hereinafter described in detail in conjunction with embodiments. Referring to FIG. 1, an electronic sphygmomanometer for use in medical clinic offices or hospitals in one embodiment of the invention is formed of a main body 20 and an armband (cuff) 30. Main body 20 includes, in addition to display units such as a systolic pressure display unit 10a, a diastolic pressure display unit 10b, a pulse rate display unit 10c and the like, keys such as a power switch 1, a pressurization switch 2 and a stop switch 13 as well as a pressurization target value setting dial 14, a successive measurement interval setting dial 15 and a pressure release rate adjustment dial 21. Although the electronic sphygmomanometer further includes many key switches and displays in addition to those shown in FIG. 1, they are not directly related to the present invention and individual description is not presented here.

Figure 2:
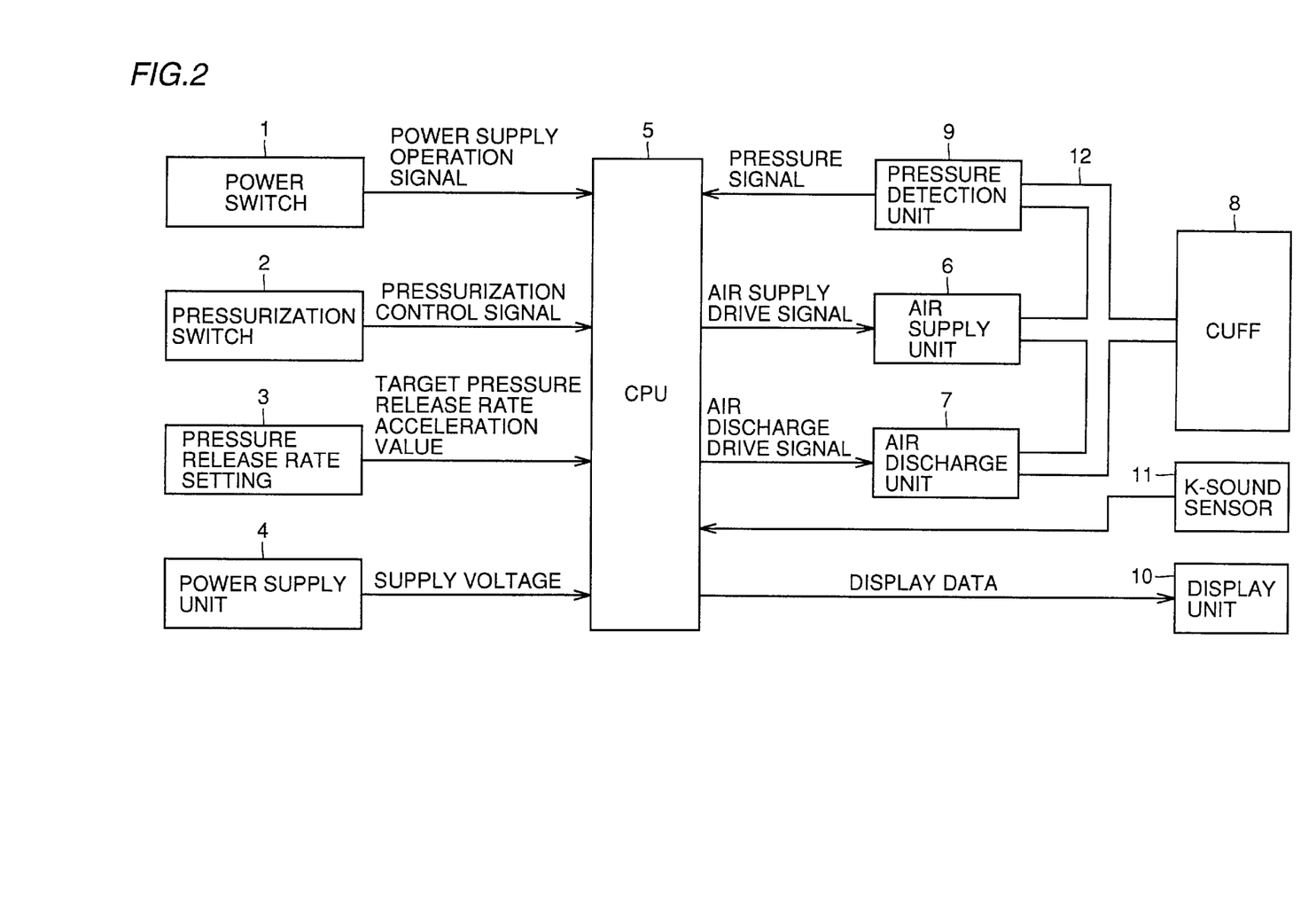
FIG. 2 is a block diagram showing an internal circuit structure of the electronic sphygmomanometer in the embodiment above.

FIG. 2 is a block diagram showing a circuit structure of the electronic sphygmomanometer in this embodiment. The electronic sphygmomanometer in this embodiment includes power switch 1, pressurization switch 2, a pressure release rate setting unit 3, a power supply unit 4, a CPU 5, an air supply unit 6 for applying air pressure to a cuff, an air discharge unit 7 for discharging the air from the cuff to release the air pressure, cuff 8, a pressure detection unit 9 for detecting the air pressure of cuff 8, a display unit 10 for displaying data such as systolic and diastolic pressures and the like, a K-sound sensor 11, and an air passage 12 communicating with air supply unit 6, air discharge unit 7, cuff 8 and pressure detection unit 9. Some of keys, dials and the like in FIG. 1 are not shown in FIG. 2.

After a decompression process starts, pressure release rate setting unit 3 outputs a standard pressure release rate voltage corresponding to a slow air discharge rate, on which an external control signal voltage is superimposed by dial 21 and a resultant voltage is output accordingly. The voltage from pressure release rate setting unit 3 is applied to a valve of air discharge unit 7. The valve is then opened according to the drive voltage to increase the pressure release rate.

Figure 3:
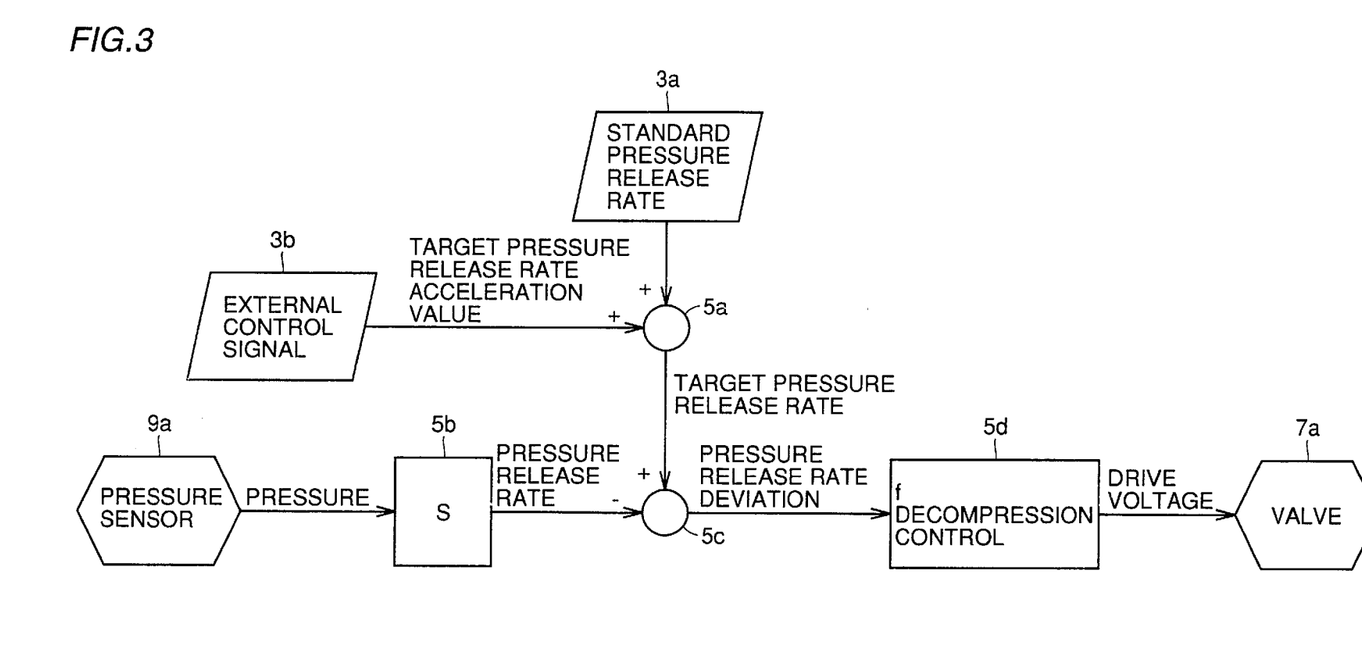
FIG. 3 is a block diagram showing a functional structure regarding control of a pressure release rate of the electronic sphygmomanometer in the embodiment above.

FIG. 3 is a functional block diagram regarding pressure release rate control of the electronic sphygmomanometer in this embodiment. A standard pressure release rate voltage 3a which is preset by pressure release rate setting unit 3 and an external control signal voltage 3b in accordance with the position of operated dial 21 are added by an adder 5a which thus outputs a target pressure release rate voltage. On the other hand, an output of a pressure sensor 9a is differentiated by a differential circuit 5b to determine a current pressure release rate. Deviation between the current pressure release rate and the target pressure release rate is determined by a subtracter 5c. Drive voltage is applied by a decompression control unit 5d to a valve 7a according to the pressure release rate deviation in order to adjust the degree of opening of the valve, and thus the pressure release rate is controlled to coincide with the target pressure release rate.

Figure 4:
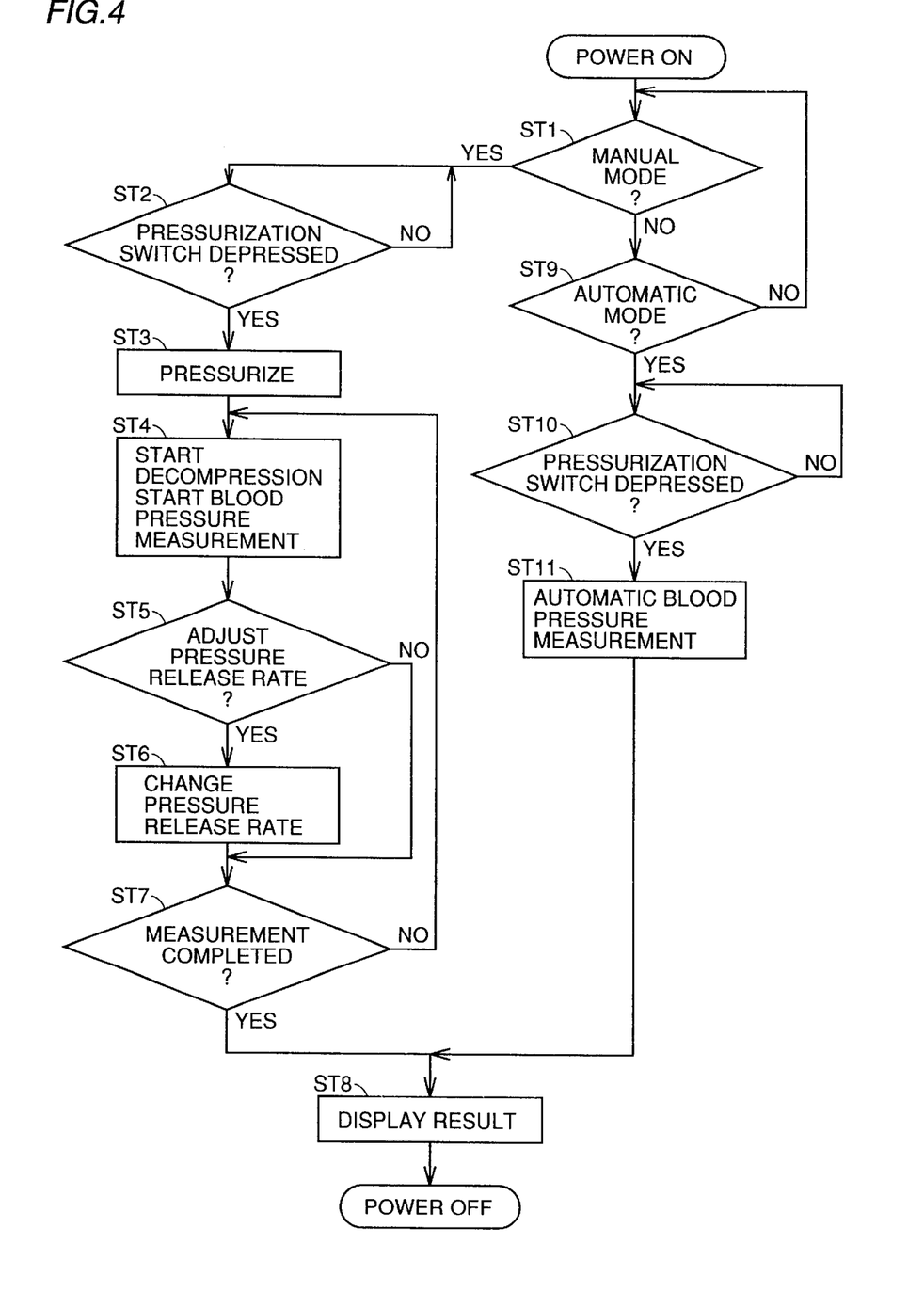
FIG. 4 is a flowchart illustrating the entire operation of the electronic sphygmomanometer in the embodiment above.

An entire operation of the electronic sphygmomanometer in this embodiment is described now in conjunction with a flowchart shown in FIG. 4. After the power is turned on by power switch 1, it is determined whether a mode setting switch selects "manual measurement" mode or "automatic measurement" mode (steps ST1 and ST9). If "manual measurement" mode is selected, depressing of pressurization switch 2 is waited for (step ST2). When pressurization switch 2 is pressed down, air pressure is applied from air supply unit 6 to cuff 8 through air passage 12 so as to start pressurization (step ST3). After the pressure is increased to a predetermined value, decompression is started (at time to in FIG. 5) in order to start measurement of blood pressure (step ST4). Dial 21 is not operated at the start of the decompression. Therefore, only the standard pressure release rate voltage is applied to valve 7a of air discharge unit 7, and the pressure is decreased at a slow pressure release rate. When K-sounds of a patient are detected by an operator who conducts measurement using a stethoscope, the cuff pressure at this time (time $t_1$ in FIG. 5) is determined as the systolic pressure (SYS). When the operator detects the K-sounds using the stethoscope, the K-sounds are detected by K-sound sensor 11 and simultaneously the blood pressure is measured by a measurement instrument. The SYS and the like determined by the sphygmomanometer may be indicated on display unit 10 or may not be indicated depending on setting.

After the systolic pressure is determined, the operator manually rotates dial 21 for increasing the pressure release rate. This corresponds to determination that the pressure release rate is to be adjusted (step ST5). The external control signal voltage determined by the position of dial 21 is added to the standard pressure release rate voltage and the resultant voltage is output from pressure release rate setting unit 3 and applied to valve 7a of air discharge unit 7. Consequently, the pressure release rate becomes faster than the standard pressure release rate (step ST6). As long as dial 21 remains at the rotated position, the pressure release rate is the fast rate obtained by changing the original rate. This state corresponds to the period $t_1$–$t_2$ in FIG. 5.

After the pressure release rate is increased to decrease the cuff pressure to the one close to the diastolic pressure, the operator returns dial 21 to its original position. In this way, only the standard pressure release rate voltage is output again from pressure release rate setting unit 3 and the pressure release rate of air discharge unit 7 becomes equal to the standard pressure release rate which is the original slow rate, at the time corresponding to $t_2$ in FIG. 5. When the operator confirms ceasing of K-sounds by the stethoscope to determine the cuff pressure at this time as the diastolic pressure, the measurement is completed (step ST7). Then, the resultant systolic and diastolic pressures are displayed (step ST8). Upon completion of the measurement, dial 21 is rotated up to full-scale to rapidly discharge the air to reduce the cuff pressure (in the period $t_2$–$t_4$ in FIG. 5).

If "automatic measurement" mode is set when the power is turned on, depressing of the pressurization switch is waited for (step ST10), and then automatic blood pressure measurement is conducted upon depressing. In this case, in the decompression process, the pressure is decreased at a constant standard pressure release rate and occurrence and ceasing of K-sounds are automatically detected to determine the systolic and diastolic pressures ($t_0$–$t_5$ in FIG. 5). As apparently understood from FIG. 5, high-speed decompression is accomplished in "manual measurement" mode in the period $t_1$–$t_2$ and thus the time for measurement is reduced by the period $t_4$–$t_6$ compared with "automatic measurement" mode. However, in "automatic measurement" mode, the degree of decompression may be enhanced automatically in the middle of measurement as implemented according to Japanese Patent Publication No. 57-5540.

Figure 6A:
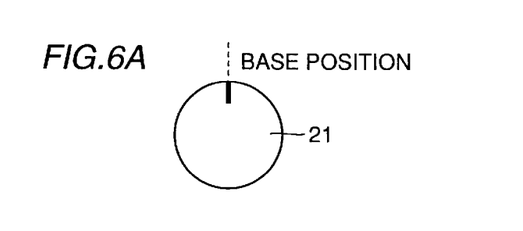
FIGS. 6A to 6C illustrate manipulation of a rotation type dial employed in the electronic sphygmomanometer in the embodiment above.

Dial 21 for adjusting the pressure release rate is located at a base position as shown in FIG. 6A when manual operation is not performed, and the pressure release rate in this case is the standard pressure release rate. When dial 21 is rotated to the position shown in FIG. 6B, the pressure release rate is increased by the voltage corresponding to the position after the rotation. When dial 21 is returned to its original position as shown in FIG. 6C, the pressure release rate becomes the standard pressure release rate. According to this embodiment, the pressure release rate never drops to the one lower than the standard pressure release rate regardless of the position of rotated dial 21 of the electronic sphygmomanometer.

Figure 7A:
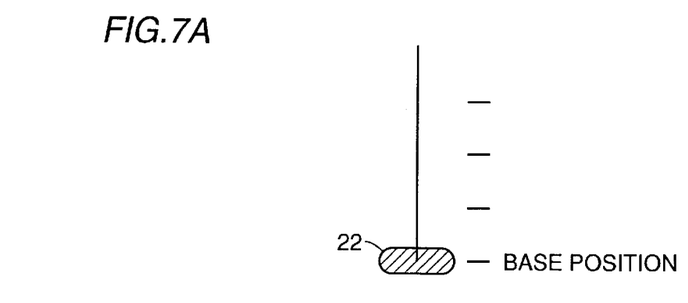
FIGS. 7A to 7C illustrate manipulation of a slide type dial for adjusting a pressure release rate employed in an electronic sphygmomanometer in another embodiment.
Figure 7B:
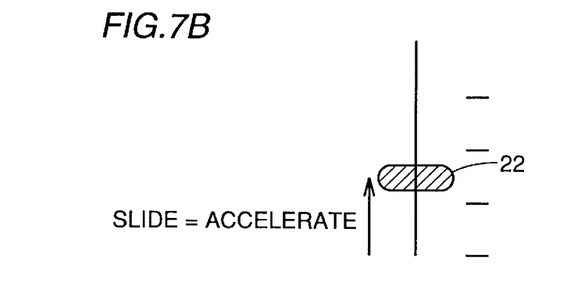
Figure 7C:
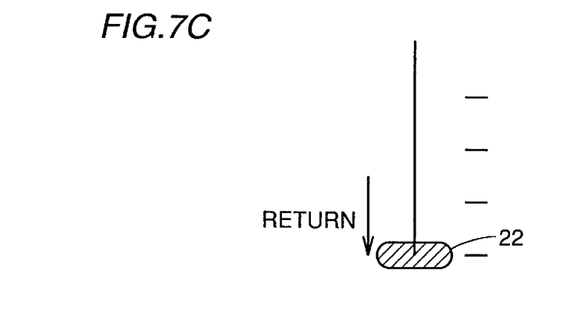

According to another embodiment, instead of pressure release rate adjustment dial 21, a slide-type dial 22 as shown in FIGS. 7A to 7C is employed. The base position shown in FIG. 7A may correspond to the standard pressure release rate. As dial 22 is moved upward as shown in FIG. 7B, the pressure release rate may be enhanced. When dial 22 is returned to the original base position as shown in FIG. 7C, the pressure release rate may become the standard pressure release rate. In this case, the pressure release rate likewise never decreases to the one below the standard pressure release rate regardless of the position of the shifted dial 22.

Restoring force in the direction of the base position may be applied preliminary by a spring or the like to dials 21 and 22 shown in FIGS. 6A to 6C and 7A to 7C. When dial 21 or dial 22 is rotated or moved upward with fingers and then held with the fingers, the dial remains at this position to increase the pressure release rate. When the fingers are released from the dial, the dial returns to the base position and accordingly the pressure release rate automatically returns to the standard pressure release rate. In this case likewise, the pressure release rate never drops to the one lower than the standard pressure release rate when the operator releases the fingers. Therefore, the operator can release the fingers without care.

Figure 6B:
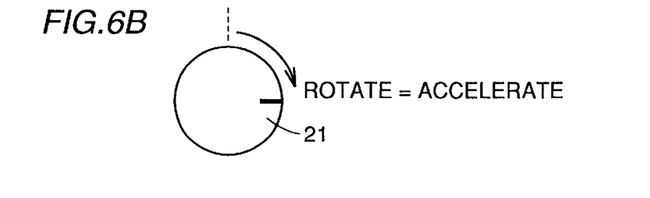
Figure 6C:
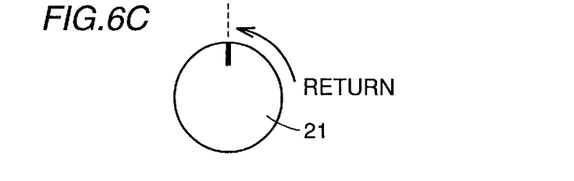
Figure 8A:
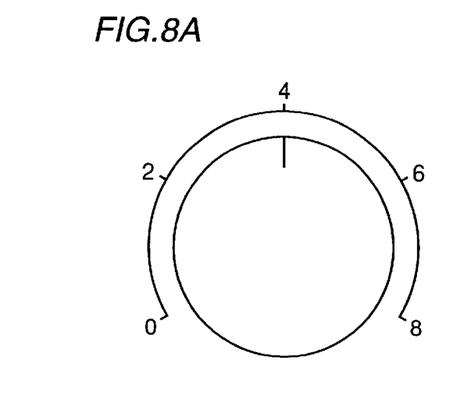
FIGS. 8A and 8B show dials for adjusting a pressure release rate employed in an electronic sphygmomanometer in still another embodiment.
Figure 8B:
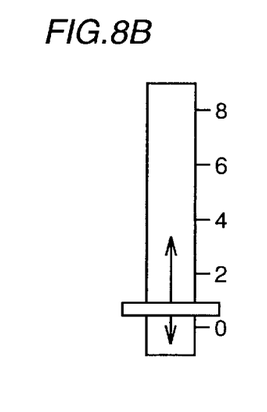

The sphygmomanometers in the embodiments above employ a dial of volume adjustment type shown in FIGS. 6A to 6C and a dial of slide type shown in FIGS. 7A to 7C. After the dials are moved according to respective types, the dials are returned to respective base positions. Alternatively, dials of the types as shown in FIGS. 8A and 8B may be employed. When fingers are released from the dials, the dials do not move to remain at that position. Then the dials are moved again in order to return them to the original position or change the rate.

Figure 9:
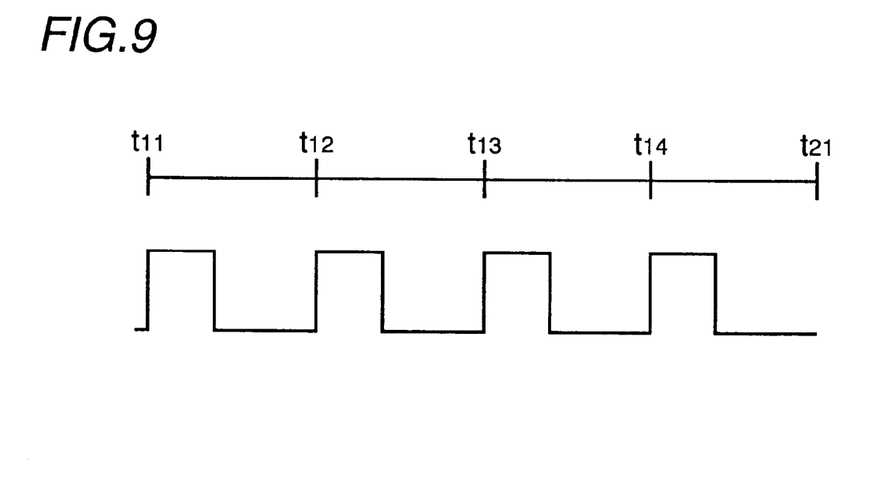
FIG. 9 shows a timing chart illustrating control of a pressure release rate by stepwise control of the electronic sphygmomanometer in the above embodiment.
Figure 10:
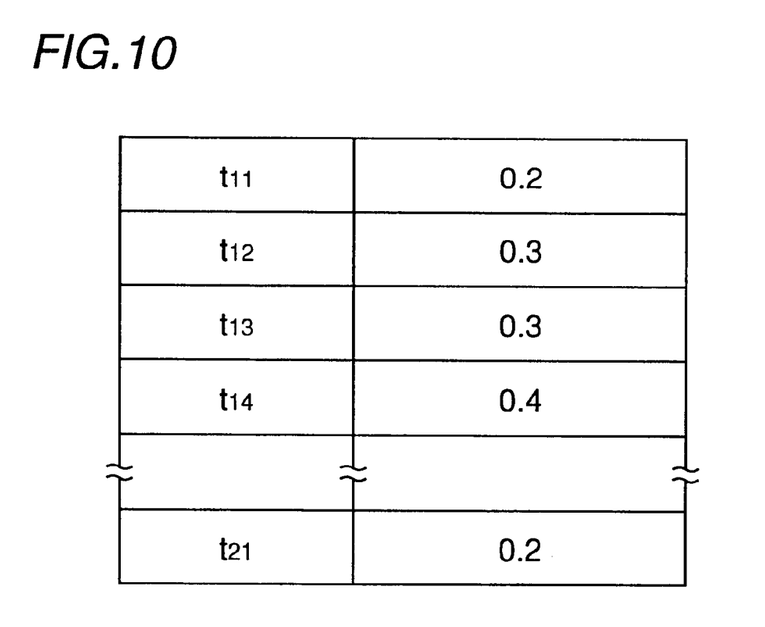
FIG. 10 shows a table used in the pressure release rate control by the stepwise control.

According to the embodiments above, the sphygmomanometer controls the decompression by externally setting the dial or the like so as to control the target rate. Alternatively, the air discharge time may be controlled by a stepwise air discharge. For example, in order to increase the pressure release rate in the period $t_1$–$t_2$ in FIG. 5, for example, the air vent valve is made ON at regular intervals $t_{11}, t_{12}, \ldots, t_{21}$ as shown in FIG. 9, with one of duties at each time. In this case, the duty of the air vent valve is naturally set greater than the one before high-speed air discharge is started. In some cases, the time when the air vent valve is made ON may be changed as time advances, or the ON time of the air vent valve may be unchanged and the period between consecutive ON times may be changed. Each ON time or each period of the air vent valve may be stored in a table following the advance of time as shown in FIG. 10. The data held in the table may be flow rate or voltage instead of the ON time and period.

A method of controlling the air discharge may be employed, as another method of controlling the decompression, according to which a key switch is made ON at a required cuff pressure to start a predetermined high-speed air discharge, the high-speed decompression is continued during ON period of the key switch, and then the key switch is made OFF to set the pressure release rate at the normal pressure release rate. Alternatively, the high-speed decompression may be done automatically in response to ON of a key switch in order to reduce the current cuff pressure to the one lower than the current pressure by a predetermined value and thereafter the pressure release rate may be returned to the normal one.

Figure 11:
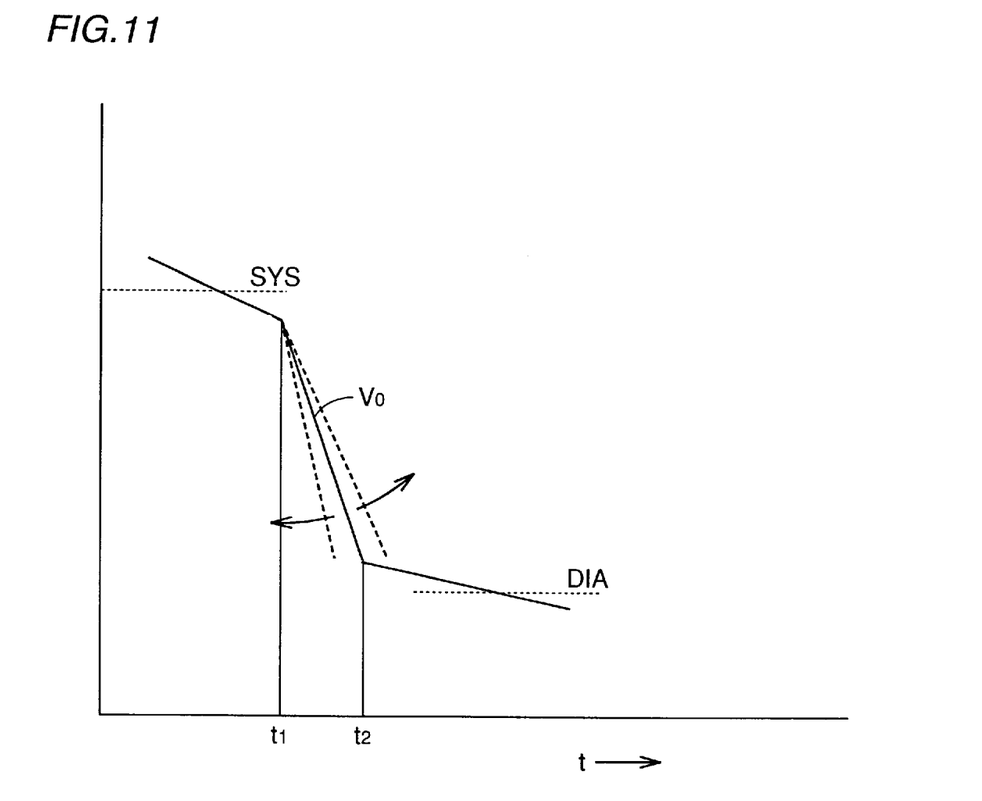
FIG. 11 illustrates another pressure release rate control.
Figure 12:
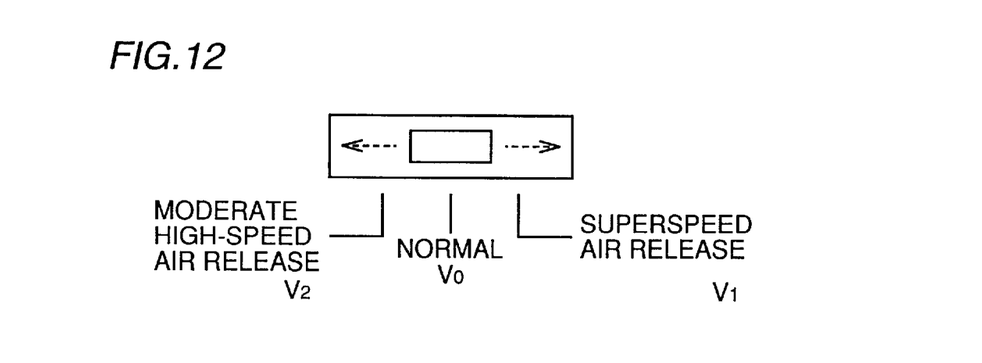
FIG. 12 shows a switch used in the pressure release rate control shown in FIG. 11.

Another decompression control may be employed, as shown in FIGS. 11 and 12, according to which high-speed decompression may be performed at a normal pressure release rate $V_0$ from time $t_1$ to time $t_2$ (or until predetermined cuff pressure is attained) after detection of K-sounds corresponding to the systolic pressure SYS, or a superspeed decompression switch may be selected to reduce the pressure at a pressure release rate $V_1$ ($V_1 > V_0$) for accomplishing decompression faster than the normal decompression, or a moderate high-speed decompression switch may be selected to reduce the pressure at a pressure release rate $V_2$ ($V_2 < V_0$) for performing decompression at a slightly slower rate than the normal rate.

Figure 13:
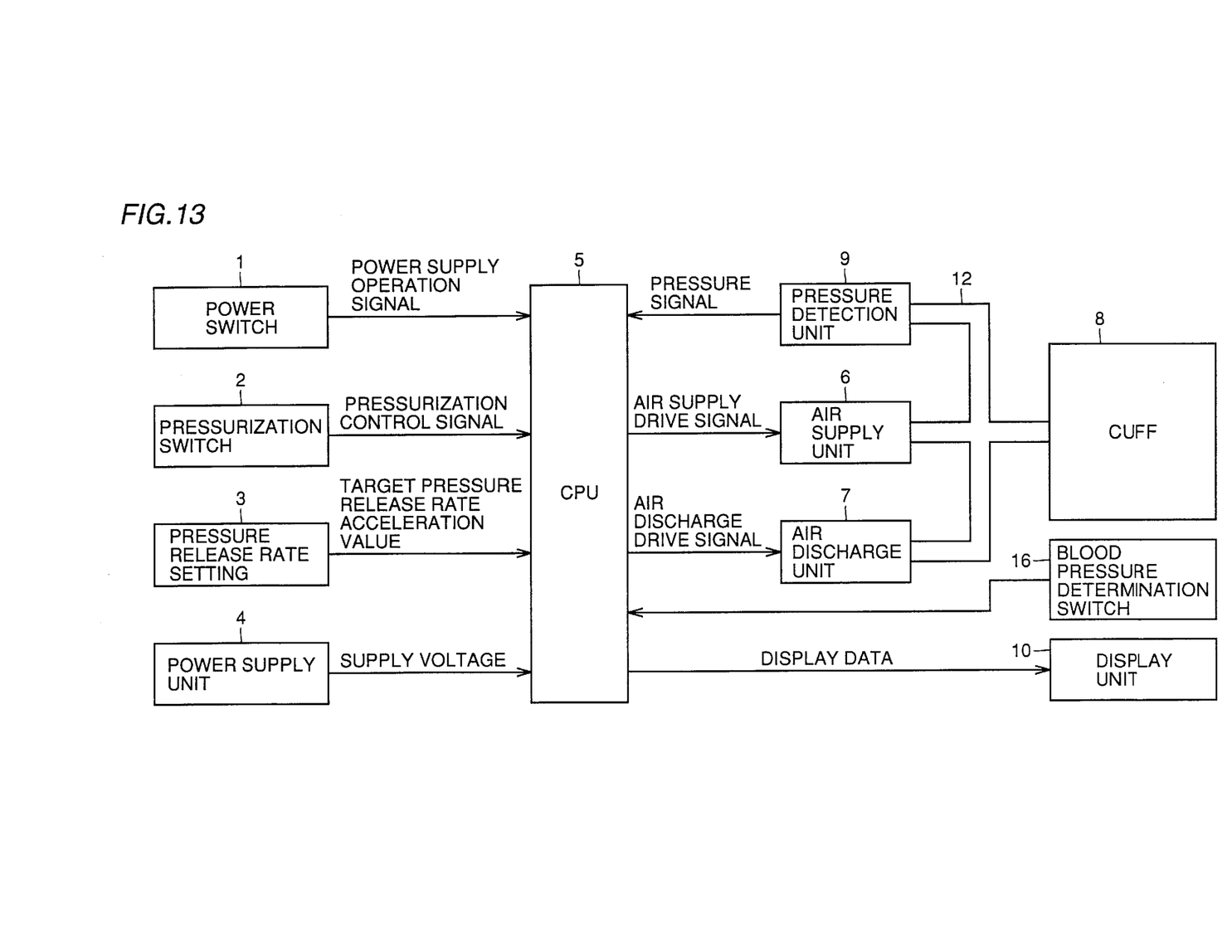
FIG. 13 is a block diagram showing a structure of a main body of an electronic sphygmomanometer in a further embodiment of the present invention.

FIG. 13 is a block diagram showing a main body of an electronic sphygmomanometer according to a further embodiment of the invention. The electronic sphygmomanometer in this embodiment includes a blood pressure determination switch 16. The electronic sphygmomanometer shown in FIG. 1 includes K-sound sensor 10 and the signal from K-sound sensor 10 is taken by CPU 5 while the electronic sphygmomanometer in this embodiment does not include K-sound sensor 10.

A power switch 1 of this electronic sphygmomanometer is first turned on and then a pressurization switch 2 is turned on. Accordingly, pressurization is started by an air supply unit 6 under control by a CPU 5 and thus the pressure of a cuff 8 increases. After the pressure increases to a predetermined cuff pressure, supply of air by air supply unit 6 is stopped and the air in the cuff is discharged at a slow rate by an air discharge unit 7 to gradually reduce the pressure. An operator who conducts measurement (physician or the like) then detects K-sounds in the decompression process using a stethoscope and turns on blood pressure determination switch 16 when the first K-sound is detected. The cuff pressure at this time which is supplied from a pressure detection unit 9 to CPU 5 is determined as the systolic pressure and this pressure is stored in a memory of CPU 5 and indicated on a display unit 10.

After this, similarly to the sphygmomanometer shown in FIG. 1, a predetermined high-speed air release is performed, the air is thereafter discharged at a slower rate again and then ceasing of K-sounds is detected. When the ceasing of K-sounds is detected, the operator turns on blood pressure determination switch 16. The cuff pressure at this time is supplied from pressure detection unit 9 to CPU 5 and determined as the diastolic pressure to be stored in the memory and indicated on display unit 10.

The electronic sphygmomanometer in this embodiment can measure blood pressure with high precision by a simple structure. In addition, the sphygmomanometer can be operated easily by any person since the highspeed air release is done electronically in an automatic or manual manner after the systolic pressure is determined while the conventional sphygmomanometer adjusts the pressure release rate manually by rotating the dial.

The various decompression control methods described above can be employed in the electronic sphygmomanometer in this embodiment. Although the main body of the electronic sphygmomanometer does not necessarily have an automatic blood pressure measuring function according to oscillometry, if the sphygmomanometer is provided with the automatic blood pressure measuring function, calibration is possible by comparison between the result of automatic measurement and blood pressure value determined by operation of blood pressure determination switch 16.

Figure 14:
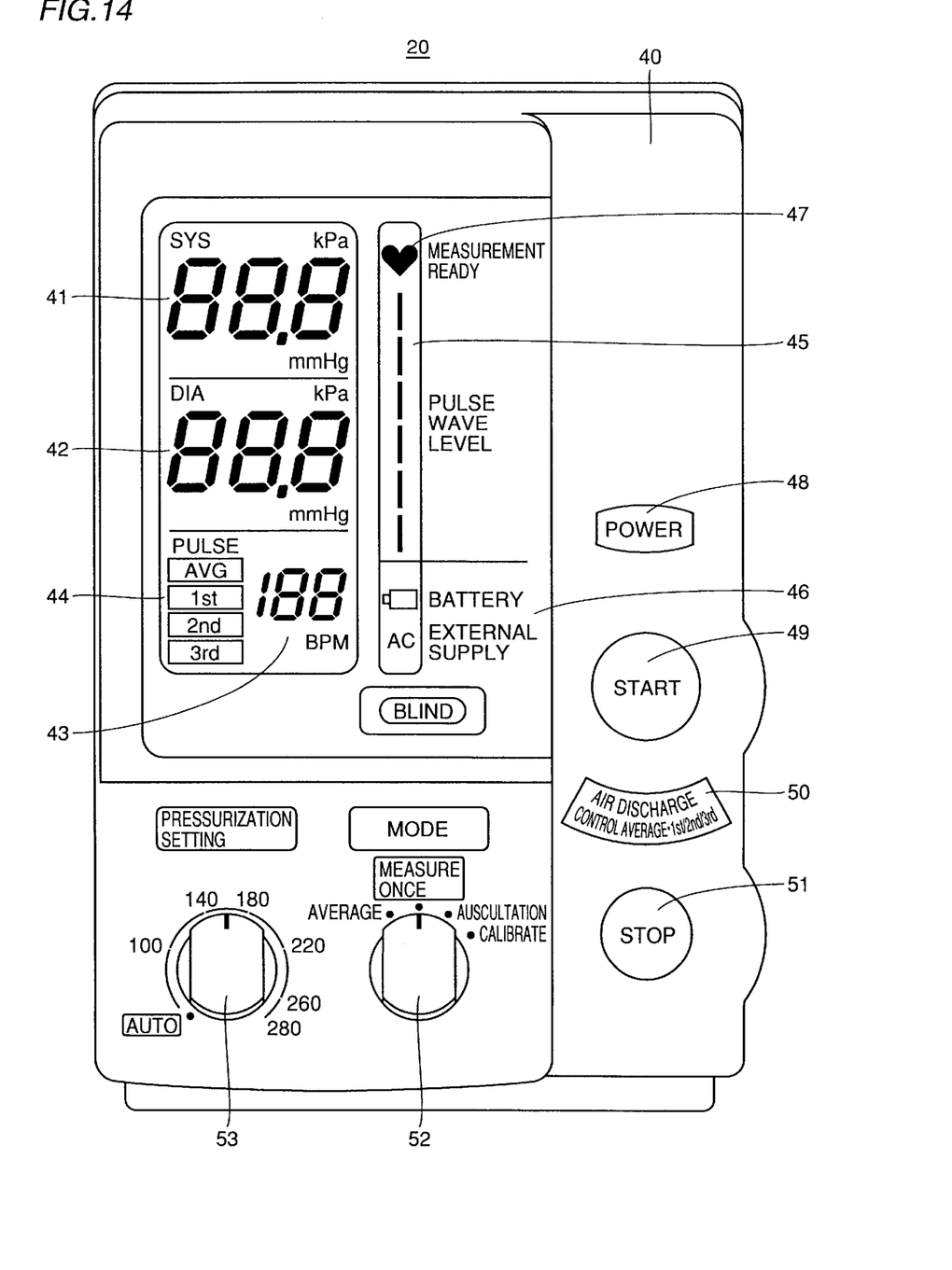
FIG. 14 shows the front part of a main body of an electronic sphygmomanometer in a further embodiment of the invention.

FIG. 14 shows a front part 40 of a main body 20 of an electronic sphygmomanometer for use in medical clinic offices or hospitals in a further embodiment of the invention. The electronic sphygmomanometer in this embodiment also includes an armband portion 30 (not shown) similar to that of the electronic sphygmomanometer in FIG. 1.

There are provided on front part 40 of main body 20, in addition to display units such as a systolic pressure display unit 41, a diastolic pressure display unit 42, a pulse rate display unit 43, a display unit 44 indicating how many times the pulse rate is measured, a pulse wave level display unit 45, an indicator 46 showing whether the power source is a rechargeable battery or external power supply, an indicator 47 indicating that preparation for measurement is completed, and the like, a group of button switches such as a power switch 48, a start switch 49, an air discharge control switch 50, and a stop switch 51 as well as a mode switch dial 52 and a pressurization setting dial 53.

By mode switch dial 52, each of the modes "measure once," "average," "auscultation" and "calibration" can be selected. By pressurization setting dial 53, any of target values of pressurization "100," "140," "180," "220," "260" and "280" and "automatic" can be set. For example, if pressurization setting dial 53 is set at "automatic" and mode switch dial 52 is set at "measure once," blood pressure is measured once by automatic pressurization and automatic decompression after start switch 49 is turned on when power switch 48 is ON.

Figure 5:
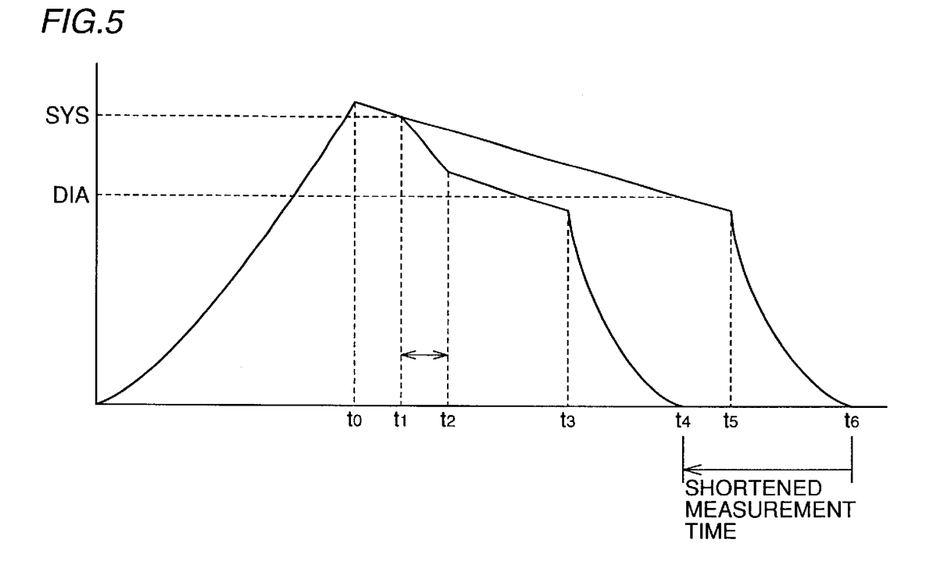
FIG. 5 shows change of cuff pressure in "manual measurement" mode and "automatic measurement" mode of the electronic sphygmomanometer in the embodiment above.

If mode switch dial 52 is set at "auscultation," similarly to "manual measurement" described in conjunction with the embodiment above, an operator who conducts measurement places a stethoscope on the artery to listen to K-sounds while the operator can manipulate air discharge control switch 50 when the K-sounds are detected in order to accomplish the highspeed decompression as done in the period $t_1$–$t_2$ shown in FIG. 5. Here, air discharge control switch 50 enables the air discharge to be controlled in the four stages, that is, average, first, second and third. Instead of this air discharge control switch, the manual operation unit as shown in FIGS. 6, 7, 8 and the like may be employed in order to electronically control the pressure release rate by manual operation.

When mode switch dial 52 is set at "average," blood pressure is successively measured three times, for example, and the average of the resultant measurements is determined as a measured blood pressure.

Figure 15:
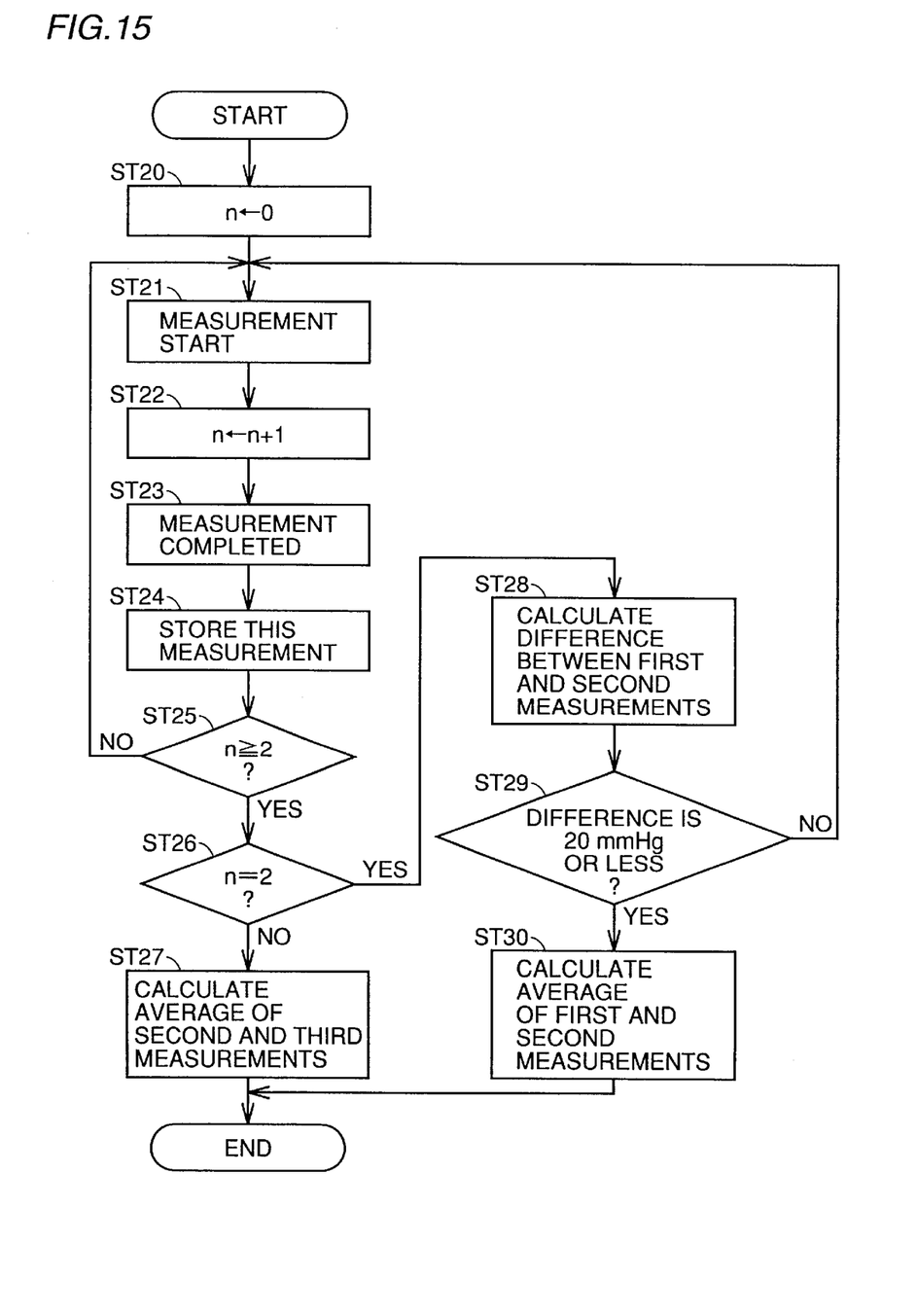
FIG. 15 is a flowchart illustrating an operation of an electronic sphygmomanometer in a further embodiment of the invention.

FIG. 15 is a flowchart illustrating an electronic sphygmomanometer according to a further embodiment of the invention. Using this electronic sphygmomanometer, values obtained by the first and second measurements for the same subject are calculated and then it is determined, based on the result of the calculation, whether the third measurement will be conducted.

In general, when the blood pressure of an outpatient is successively measured, the first measurement value is sometimes high. This occurs when the subject gets nervous or the subject comes to the hospital by walk and immediately undergoes measurement of blood pressure, for example. In such a case, the first measurement value is discarded and the second and third measurement values are employed in the actual medical site in order to accurately determine the blood pressure. However, in the current medical status, calculation and determination of blood pressure which are done by a nurse are troublesome and the determination could vary depending on a person who determines. In order to solve this problem, whether the third measurement is performed or not is automatically determined in this embodiment.

When an operation is started, variable n is cleared at first (step ST20) to start the first measurement (step ST21). Then, variable n is incremented by 1 (step ST22). N=1 because N=0 at the time of start. This measurement or the first measurement is completed (step ST23). This (first) measurement value is stored (step ST24). Following this, whether variable n is 2 or more is determined (step ST25). Because n=1, the answer is NO and step ST21 is performed again after a predetermined time to start the second measurement (step ST21). Variable n is incremented by 1 (step ST22) and the variable is now equal to 2. After the measurement is completed (step ST23), this or the second measurement result is stored (step ST24). It is thereafter determined whether n is 2 or more (step ST25). Since n is equal to 2 this time, the answer in step ST25 is YES and step ST26 is performed.

Determination is made as to whether n is equal to 2 or not in step ST26. The answer is also YES and the difference between the first and second measurement values is calculated (step ST28). Then it is determined whether this calculation result (difference) is equal to or less than a preset standard, 20 mmHg in this example (step ST29). If the first measurement value is great and the difference exceeds 20 mmHg, the answer in step ST29 is NO and step ST21 is performed to start the third measurement. In the third measurement, processes from the start to step ST26 are similar to those in the second measurement. However, the answer in step ST26 is NO because of n=3. Therefore, the first measurement value is not employed and the average of the second and third measurement values is calculated (step ST27) and the operation is completed.

If the result (difference) in step ST29 is 20 mmHg or less, the third measurement is unnecessary. Then, the average of the first and second measurement values is calculated (step ST30) and the operation is completed.

Although the present invention has been described and illustrated in detail, it is clearly understood that the same is by way of illustration and example only and is not to be taken by way of limitation, the spirit and scope of the present invention being limited only by the terms of the appended claims.

What is claimed is:

1. An electronic sphygmomanometer applying pressure to a cuff for pressurizing blood vessel and measuring blood pressure in a decompression process, comprising:

decompression means for releasing the pressure from the cuff;

pressure release rate control means for controlling a pressure release rate at which said decompression means reduces the pressure; and manual operation means for electrically controlling said pressure release rate control means in response to a manual operation of the manual operation means;

wherein said manual operation means increases the pressure release rate from a first predetermined rate to a second predetermined rate in response to a start of the manual operation and decreases the rate from the second predetermined rate to a third predetermined rate in response to an end of the manual operation, said second predetermined rate being greater than the first rate or the third rate.

2. The electronic sphygmomanometer according to claim 1, further comprising mode switch means for switching between a manual measurement mode and another measurement mode, wherein when the manual measurement mode is selected, said pressure release rate control means is electronically controlled in response to manual operation of said manual operation means.

3. The electronic sphygmomanometer according to claim 1, wherein said pressure release rate control means includes an air vent valve for reducing the pressure of said cuff, and degree of opening of said air vent valve is controlled according to change of an electric signal caused by operation of said manual operation means.

4. The electronic sphygmomanometer according to claim 1 or 2, wherein said pressure release rate control means starts the decompression process at the first predetermined pressure release rate and thereafter increases the pressure release rate to the second predetermined pressure release rate upon the manual operation of said manual operation means.

5. The electronic sphygmomanometer according to claim 1, 2 or 3, wherein the first predetermined rate and the third predetermined rate are substantially the same.

6. An electronic sphygmomanometer comprising:

a cuff for pressurizing blood vessel;

pressurization means for applying pressure to said cuff;

cuff pressure detection means for detecting the pressure of said cuff;

air discharge means for discharging air from said cuff to release the pressure from said pressurized cuff;

display means for displaying the pressure of said cuff;

manual operation means for electronically controlling said air discharge means in response to its manual operation; and adjustment means for adjusting degree of discharging air by said air discharge means by operation of said manual operation means.

* * * * *